United States Patent [19]
Voelskow et al.

[11] Patent Number: 4,467,034
[45] Date of Patent: Aug. 21, 1984

[54] **PROCESS FOR THE PRODUCTION OF D-LACTIC ACID WITH THE USE OF *LACTOBACILLUS BULGARICUS* DSM 2129**

[75] Inventors: Hartmut Voelskow, Hattersheim am Main; Dieter Sukatsch, Frankfurt am Main, both of Fed. Rep. of Germany

[73] Assignee: Hoechst Aktiengesellschaft, Frankfurt am Main, Fed. Rep. of Germany

[21] Appl. No.: 406,473

[22] Filed: Aug. 9, 1982

[30] Foreign Application Priority Data

Aug. 11, 1981 [DE] Fed. Rep. of Germany ....... 3131717

[51] Int. Cl.$^3$ .......................... C12P 7/56; C12N 1/20; C12R 1/225
[52] U.S. Cl. ..................................... 435/139; 435/253; 435/853
[58] Field of Search ........................ 435/139, 853, 253

[56] References Cited

U.S. PATENT DOCUMENTS 3,988,440 10/1976 Bogdanov ........................... 435/853
4,156,019 5/1979 Kondratenkov et al. .......... 435/853

OTHER PUBLICATIONS

Tiwari et al., Proc. Nat. Acad. Sci. India, 47(A) II, pp. 130–132, (1977).
VO über diätetische Lebensmittel ("Regulations on Dietetic Foodstuffs"), Federal Republic of Germany.
Biochemie der Ernährung ("Biochemistry of Nutrition"), Steinkopff Verlag, Darmstadt 1979, pp. 46–48.

*Primary Examiner*—Alvin E. Tanenholtz
*Attorney, Agent, or Firm*—Curtis, Morris & Safford

[57] ABSTRACT

D-lactic acid is obtained by fermentation of a nutritive medium containing glucose and/or lactose and other usual additives by means of *Lactobacillus bulgaricus* DSM 2129.

10 Claims, No Drawings

PROCESS FOR THE PRODUCTION OF D-LACTIC ACID WITH THE USE OF *LACTOBACILLUS BULGARICUS* DSM 2129

A process for the fermentative production of D-lactic acid is known from British Pat. No. 1,157,213. The *Lactobacillus leichmanii* ATCC 4797 used in this process can form within 60 hours 113 g of D-lactic acid per liter of nutritive medium, the nutrient containing either glucose or beet sugar molasses and other usual additives.

In view of the increasing demand for D-lactic acid as a starting material for the chemical synetheses of optically active compounds, it was the object of the invention to develop a more efficient process for obtaining the acid, which process would especially decrease fermentation time and employ a microorganism utilizing not only glucose and beet sugar molasses but also lactose which, is available in large amounts in whey. This object has been achieved by means of *Lactobacillus bulgaricus*.

*Lactobacillus bulgaricus* is known for being capable of an especially rapid fermentation due to its considerable metabolic activity. It is therefore used for yoghurt production, where it completes the milk fermentation within 4 hours. However, the strains of *Lactobacillus bulgaricus* existing in nature and in fermented milk cannot produce more than 25 to 30 g of lactic acid per liter of medium. More than half of the lactose present remains unfermented.

In an acidified milk sample, there has been found surprisingly a strain of *Lactobacillus bulgaricus* the efficiency of which could be improved by systematic selection in such a manner that it is capable of forming up to 115 g of lactic acid per liter of medium. This strain was identified as consisting of long gram-positive rods which are catalase-negative, motionless and microaerophilic, and do not have spores. Furthermore, it has the following characteristics:

| Metabolism: | homofermentative lactic acid fermentation |
|---|---|
| Gas from glucose: | − |
| Gas from gluconate: | − |
| Growth at 15° C.: | − |
| Growth at 45° C.: | − |
| Acid formation from ribose: | − |
| arabinose: | − |
| xylose: | − |
| mannitol: | − |
| sorbitol: | − |
| glucose: | + |
| galactose: | − |
| lactose: | + |
| maltose: | − |
| saccharose: | − |
| trehalose: | − |
| cellobiose: | − |
| melibiose: | − |
| raffinose: | − |
| salicin: | − |
| amygdalin: | − |
| Arginine splitting: | |
| Configuration of lactic acid: | D(−) |
| Diaminopimelic acid in the cell wall: | none |

This strain was registered in the German Collection of Microorganisms (Deutsche Sammlung für Mikroorganismen) as DSM 2129. It is one object of this invention.

The novel strain of *Lactobacillus bulgaricus* is capable of forming up to 115 g of D-lactic acid per liter of medium within 48 hours. Moreover, it is not specialized for fermentation of glucose, but can ferment lactose to lactic acid nearly as fast as glucose. Thus, the whey available in large quantities as a waste product of the dairy industry can be utilized as raw material source for the production of D-lactic acid.

A further object of the invention is therefore a process for the production of D-lactic acid by anaerobic fermentation of a nutritive medium containing glucose and/or lactose and other usual additives, wherein *Lactobacillus bulgaricus* DSM 2129 is used as lactic acid producing microoganism. The lactose is used generally in the form of whey or a suspension of whey powder to which glucose, too, may optionally be added.

The nutritive media used for obtaining D-lactic acid are made up in a known manner. In addition to glucose and/or lactose they must further contain a nitrogen source, for example meat extract, cornsteep or soybean flour. Mineral salts, vitamins and surface-active agents are also added. Suitable surface-active agents are especially commercial nonionic surfactants, especially liquid products. The agents generally contain polyoxalkylates as an active ingredient, such as reaction products of alcohols or acids with ethylene oxide and/or propylene oxide. Suitable alcohols are mono- or polyhydric alcohols such as fatty alcohols, resin alcohols, glycerol, erythritol, or pentaerythritol, or sugar alcohols such as sorbitol or mannitol; suitable acids are above all fatty or resinic acids. Furthermore, partial esters of such polyols and the cited acids, for example oxethylates of an anhydrosorbitol-monooleate are advantageous.

Since *Lactobacillus bulgaricus* DSM 2129 is sensitive to acids, the lactic acid produced must be bound by alkali or alkaline earth metal hydroxides or carbonates, especially calcium carbonate, so that the pH is maintained in the range of from 4.5 to 7, preferably 6.5 to 6.8.

Each nutritive medium should be sterilized before inoculation with *Lactobacillus bulgaricus* DSM 2129 in order to suppress possible contamination by foreign organisms. This is ensured by heating the medium for 15 minutes to 121° C.

As in all lactic acid fermentations, anaerobic conditions also have to be maintained in the process of the invention, for which purpose the carbon dioxide formed by neutralization of the lactic acid with calcium carbonate, or a nitrogen blanket over the fermentation medium are sufficient.

The lactic acid fermentation can be carried out at a temperature in the range from 30° C. to 50° C. A temperature of 40° C. to 45° C. is especially favorable.

From the salt of D-lactic acid obtained in the process of the invention, the free D-lactic acid can be isolated by ion exchange or, in the case of calcium lactate, by acidification with sulfuric acid.

The following Examples illustrate the invention. Percentages are by weight unless otherwise stated.

EXAMPLE 1

Development of the Lactobacillus DSM 2129 strain

The Lactobacillus strain found in a sample of fermented milk was isolated and cultivated on the following medium 1 (all indications in g/l):

| | |
|---|---|
| casein peptone (tryptic digestion) | 10 |
| meat extract (Merck) | 10 |
| yeast extract | 5 |
| glucose | 20 |

| -continued | |
|---|---|
| K$_2$HPO$_4$ | 2 |
| sodium acetate | 5 |
| MgSO$_4$.7H$_2$O | 0.2 |
| MnSO$_4$.H$_2$O | 0.05 |
| nonionic surfactant | 1 ml/l |

Subsequently, samples of the strain were diluted and inoculated onto agar plates prepared from the same medium with an addition of 1.8% of agar. The inoculated agar plates were then kept for 1 day at 45° C. in an incubator under anaerobic conditions.

A total of 30 individual colonies were then removed and introduced each into a different culture vial containing the following medium 4 (indications of g/l):

| glucose | 50 |
|---|---|
| CaCO$_3$ | 70 |
| yeast extract | 7 |
| cornsteep (dry) | 15 |
| sodium acetate | 5 |
| nonionic surfactant | 1 ml/l |

The cultivation time was 24 hours at 45° C. After this time, the difference in fermenting behavior between the cultures was clearly proved by the amounts of D-lactic acids formed in each case. The vial having the highest content of D-lactic acid was used for a new incubation on agar plates. This was regularly repeated for 8 weeks. In this selection, the sugar content of the medium was increased first to 8% and after a further 5 weeks to 10%. The strain was then selected for a further 12 weeks until it was capable of metabolizing 65% of 100 g of glucose/l of medium within 24 hours, thus forming 55 g of D-lactic acid per liter. The glucose degradation was complete after 36 to 40 hours.

EXAMPLE 2

The *Lactobacillus bulgaricus* strain obtained according to Example 1 was inoculated into different culture vials each containing 15 ml of the medium 1. For cultivation, the vials were placed vertically for at least 8 hours to up to 20 hours at a temperature of at most 45° C., and the contents were then used as an inoculum for cultures in Erlenmeyer flasks each containing 250 ml of medium 1. These flasks were then likewise left standing for 8 to 20 hours at 45° C.

The contents of 6 individual Erlenmeyer flasks were then used as an inoculum for a fermenter having a capacity of 30 liters, into which the following medium 2 was previously introduced (indications in g/l):

| glucose | 30 |
|---|---|
| CaCO$_3$ | 15 |
| yeast extract | 7 |
| casein peptone | 10 |
| cornsteep (dry) | 25 |
| sodium acetate | 5 |
| nonionic surfactant | 1 ml/l |

The fermenter was stirred at 100 rpm/min, and after 8 to 12 hours at 45° C., the contents were introduced into a fermenter having a capacity of 270 liters and containing the medium 4 according to Example 1 or the following medium 3 (indications in g/l):

| glucose | 30 |
|---|---|

| -continued | |
|---|---|
| CaCO$_3$ | 70 |
| yeast extract | 7 |
| soybean flour | 15 |
| sodium acetate | 5 |
| nonionic surfactant | 1 ml/l |

After the culture had started to grow, that is, after about 6 to 8 hours, further glucose was added. This glucose amount to be added depended on the glucose consumption and the acid formation. A total amount of glucose was added within 40 to 50 hours which corresponds to about 10 weight % of the nutritive medium. From the glucose, 110 to 115 g of D-lactic acid/l of culture medium were formed (which corresponds to 159–166 g of calcium lactate). The free lactic acid was isolated according to known methods, that is, calcium precipitation with sulfuric acid, filtration, evaporation and purification by distillation as ethyl or methyl ester.

The use of the medium 3 has the advantage that no detectable lactic acid is present in the final product. On the other hand, medium 4 has the advantage of being considerably more easily filterable than medium 3, because the soybean flour in medium 3 is only partially degraded. A product obtained with the use of medium 4 contains from 1.5 to 2% of L-lactic acid stemming from the cornsteep in the medium.

After filtration, splitting of the L-lactic acid portion is possible by passing the filtrate through an enzyme reactor containing an enzyme which ensures specific splitting of L-lactic acid. Systems containing L-lactate-oxidase, L-lactate-dehydrogenase or cytochrome b$_2$ are suitable. L-lactate-dehydrogenase requires NAD as a cofactor, which likewise may be bound to a carrier and thus can be regenerated and reused. Hexacyanoferrate is a suitable cofactor for cytochrome b$_2$, which can be reoxidized by means of electric current on a noble metal electrode.

EXAMPLE 3

Strain culture and inoculum were prepared according to the operation mode of Example 2, but as nutritive medium, the following medium 5 was used which contained lactose as subtrate to be fermented (indications in g/l):

| whey powder | 60 |
|---|---|
| CaCO$_3$ | 70 |
| yeast extract | 3 |
| soybean flour | 5 |
| sodium acetate | 5 |
| nonionic surfactant | 1 ml/l |

As in Example 2, after the culture had started to grow the sugar substrate was after-dosed until the lactose amount added in total was 130 g/l of medium. Lactic acid formation took slightly more time than in Example 2; it was however complete after 45 to 55 hours. In all other respects, the mode of operation was as described in Example 2.

EXAMPLE 4

Strain culture and inoculum were prepared under a nitrogen blanket as indicated in Example 1. The media 3, 4 or 5 were used, but they contained no CaCO$_3$ from the start; it was added later either in dry form or as a 20% suspension, so that the pH never decreased below 5.5. After 48 hours, addition of the nutritive solution was started. The dilution rate was first 0.01 l/h per l of nuturitive solution, while an identical amount of liquid was constantly removed from the fermenter. Subsequently, the dilution rate was slowly increaded up to 0.03 to 0.04 l/h per l of nutritive solution, while the off-stream from the fermenter contained a D-lactic acid content of 5 to 7%. The cell mass was separated from the off-stream by means of a continuous separator, and 90% thereof were recycled to the fermenter. The supernatant was adjusted to pH 6.5 by means of calcium hydroxide, and evaporated to about 1/10 of its initial volume. In a cooling trap, the concentrate was cooled to 4° C., thus causing the calcium lactate to crystallize. The concentrated solution flowed continuously into the cooling trap, while the precipitated calcium lactate was discharged in regular intervals by means of a slider. The mother liquor was recycled to the fermenter. The lactic acid was isolated from the calcium lactate obtained by means of sulfuric acid and subsequent filtration.

EXAMPLE 5

Continuous lactic acid preparation according to Example 4 was repeated, with the difference however that not $CaCO_3$ but sodium hydroxide was used for adjusting the pH. The advantage of this mode of operation is that a pH of 6.5 to 6.8 can be maintained, which inreases the fermenting rate of *Lactobacillus bulgaricus* DSM 2129. The sodium lactate solution obtained was led through ion exchanger columns which adsorbed the lactic acid. As soon as a column was loaded with lactic acid, it was eluted with hydrochloric acid. After regeneration with dilute sodium hydroxide solution, the column could be reused for lactic acid adsorption.

What is claimed is:

1. A process for producing D-lactic acid which comprises anaerobically fermenting a nutritive medium comprising glucose, lactose, or both, with *Lactobacillus bulgaricus* DSM 2129.
2. The process as claimed in claim 1, wherein whey or a suspension of whey powder is used as nutritive medium.
3. The process as claimed in claim 2, wherein glucose is added to the nutritive medium.
4. The process as claimed in claim 1, wherein the fermentation is carried out at temperatures of from 30° to 50° C.
5. The process as claimed in claim 1, wherein the fermentation is carried out at 40° C. to 45° C.
6. The process as claimed in claim 1, wherein the fermentation is carried out at a pH from 4.5 to 7.
7. The process as claimed in claim 1, wherein the fermentation is carried out at a pH from 6.5 to 6.8.
8. The process as claimed in claim 1, wherein calcium carbonate is added to the nutritive medium.
9. The process as claimed in claim 1, wherein the operations are carried out under a protective gas atmosphere.
10. A biologically pure culture of *Lactobacillus bulgaricus* DSM 2129 capable of producing 115 grams of lactic acid per liter of medium within 48 hours.

* * * * *